US009044625B2

(12) United States Patent
Palacharla et al.

(10) Patent No.: US 9,044,625 B2
(45) Date of Patent: Jun. 2, 2015

(54) PIEZO DRIVER HAVING LOW CURRENT QUIESENT OPERATION FOR USE IN A PERSONAL ALERT SAFETY SYSTEM OF A SELF-CONTAINED BREATHING APPARATUS

(71) Applicant: Honeywell International Inc., Morristown, NJ (US)

(72) Inventors: Praveen Kumar Palacharla, Andhra Pradesh (IN); Kanthimathinathan T, Karnataka (IN); Neeraj Kumar Rai, Rajasthan (IN)

(73) Assignee: Honeywell International Inc., Morristown, NJ (US)

( * ) Notice: Subject to any disclaimer, the term of this patent is extended or adjusted under 35 U.S.C. 154(b) by 395 days.

(21) Appl. No.: 13/663,010

(22) Filed: Oct. 29, 2012

(65) Prior Publication Data

US 2014/0116431 A1 May 1, 2014

(51) Int. Cl.

| | |
|---|---|
| ***A61M 11/00*** | (2006.01) |
| ***A62B 9/00*** | (2006.01) |
| *A62B 25/00* | (2006.01) |
| *A62B 21/00* | (2006.01) |
| *A62B 7/02* | (2006.01) |

(52) U.S. Cl.

CPC ................. *A62B 9/006* (2013.01); *A62B 25/00* (2013.01); *A62B 21/00* (2013.01); *A62B 7/02* (2013.01)

(58) Field of Classification Search

CPC ........ A62B 25/00; A62B 21/00; A62B 9/006; A62B 7/00

USPC ............. 128/205.22, 200.24, 204.18, 204.21, 128/205.23; 116/137 R, 137 A, 147; 340/850, 384.6

See application file for complete search history.

(56) References Cited

U.S. PATENT DOCUMENTS

| | | | | |
|---|---|---|---|---|
| 3,600,612 | A * | 8/1971 | Beeken | 310/322 |
| 3,875,801 | A * | 4/1975 | Bishaf | 73/714 |
| 4,393,373 | A * | 7/1983 | Torii et al. | 340/384.6 |
| 4,737,343 | A | 4/1988 | Hirschfeld | |
| 5,317,305 | A | 5/1994 | Campman | |
| 5,570,688 | A * | 11/1996 | Cochran et al. | 128/205.23 |
| 5,659,296 | A | 8/1997 | Debe et al. | |
| 5,666,949 | A * | 9/1997 | Debe et al. | 128/202.22 |
| 6,016,099 | A | 1/2000 | Campman | |
| 6,091,331 | A | 7/2000 | Toft et al. | |
| 6,201,475 | B1 | 3/2001 | Stumberg et al. | |
| 6,701,864 | B2 | 3/2004 | Watson, Jr. et al. | |
| 6,853,301 | B2 | 2/2005 | Devine | |
| 6,995,659 | B2 | 2/2006 | Soto-Nicolas | |
| 7,503,962 | B2 | 3/2009 | Atar | |
| 7,592,184 | B2 | 9/2009 | Khalil et al. | |
| 2007/0235030 | A1 * | 10/2007 | Teetzel et al. | 128/205.12 |

* cited by examiner

*Primary Examiner* — Steven Douglas

(74) *Attorney, Agent, or Firm* — Conley Rose, P.C.; Kristin Jordan Harkins

(57) ABSTRACT

Embodiments relate generally to personal alert safety systems (PASS) as well as the use of piezoelectric sound generators which may be located within a PASS device operable to alert others when user is in danger. Some embodiments further relate to the use of a PASS device in an SCBA. Embodiments may also relate to the design of piezoelectric driver circuits operable to sound one or more piezoelectric sound generators, wherein the driver circuit design may be low cost and energy efficient.

20 Claims, 6 Drawing Sheets

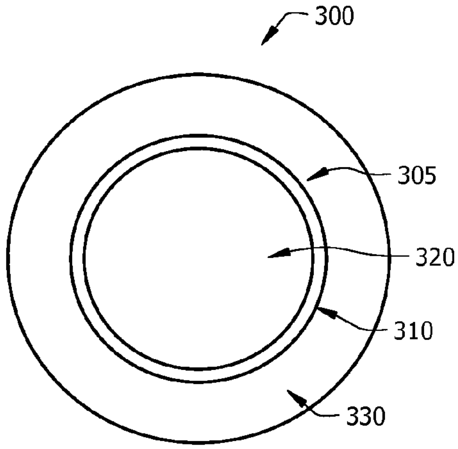
*FIG. 3A*
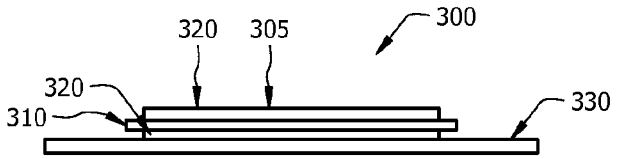
*FIG. 3B*
*FIG. 4A*
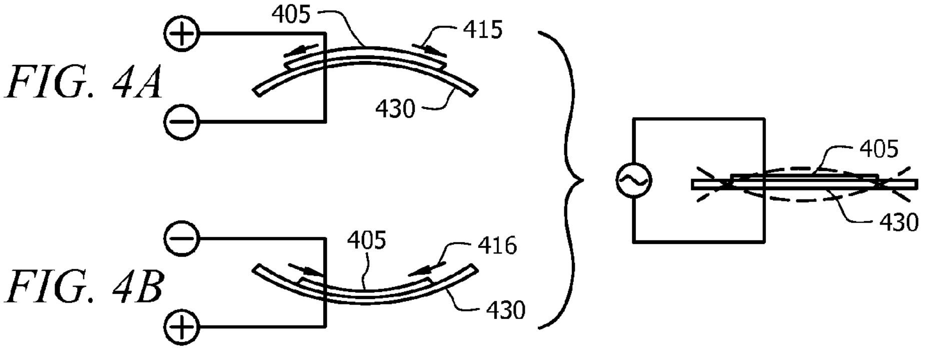
*FIG. 4B*
*FIG. 4C*

PIEZO DRIVER HAVING LOW CURRENT QUIESENT OPERATION FOR USE IN A PERSONAL ALERT SAFETY SYSTEM OF A SELF-CONTAINED BREATHING APPARATUS

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A Personal Alert Safety System (or PASS) device is commonly used by firefighters when entering a hazardous environment, such as a burning building. The PASS device is a small battery powered device that is carried with the user and will sound a loud audible alert to notify others if the user is in distress. The PASS device can, for example, be attached to a backpack style harness for a self-contained breathing apparatus (SCBA), a turnout coat or other protective clothing worn by a firefighter. Typically, a PASS device can be activated manually or automatically (for example, manually by the user pressing a button, or automatically by a motion sensing device that activates the PASS device when the user has not moved in a certain amount of time), and the device will typically not turn itself off unless it is manually reset. According to NFPA (National Fire Protection Association) 1982: 2013 standards, an activated PASS device must emit a high-pitched audible alert of at least 95 decibels at a distance of 3 meters from the device. The sound of an activated PASS device indicates a true emergency and should result in an immediate response to rescue the firefighter in distress.

SUMMARY

Aspects of the disclosure may include embodiments of a self-contained breathing apparatus (SCBA) for use by emergency responders, comprising: a backpack; a bottle of gas secured to the backpack; and a personal alert safety system (PASS). The PASS may comprise a piezoelectric sound generator, a power supply, a piezoelectric controller, and a piezoelectric driver circuit comprising a push circuit comprising a first bipolar junction transistor (BJT), a second BJT, a third transistor, a first resistor, and a second resistor, wherein the first BJT may have a base lead coupled to an output of the piezocontroller, an emitter lead coupled to ground, and a collector lead coupled to a first lead of the first resistor, to an input of the third transistor, and to a base lead of the second BJT. In an embodiment, a second lead of the first resistor may be coupled to the power supply, a power input lead of the third transistor may be coupled to the power supply and an output of the third transistor may be coupled to a first lead of the second resistor and to an emitter lead of the second BJT. In an embodiment, a second lead of the second resistor may be coupled to the piezoelectric sound generator, and the collector lead of the second BJT may be connected to ground.

In an embodiment, the piezoelectric driver circuit further comprises a pull circuit comprising a fourth BJT, a fifth BJT, a sixth transistor, a third resistor, and a fourth resistor, wherein the fourth BJT may have a base lead coupled to an output of the piezocontroller through an inverter, an emitter lead coupled to ground, and a collector lead coupled to a first lead of the third resistor, to an input of the sixth transistor, and to a base lead of the fifth BJT. In an embodiment, a second lead of the third resistor may be coupled to the power supply, a power input lead of the sixth transistor may be coupled to the power supply and an output of the sixth transistor may be coupled to a first lead of the fourth resistor and to an emitter lead of the fifth BJT. In an embodiment, a second lead of the fourth resistor may be coupled to the piezoelectric sound generator at an end opposite from the second end of the second resistor, and the collector lead of the fifth BJT may be connected to ground. In an embodiment, the third transistor may be a Darlington pair, wherein the Darlington pair may comprise two NPN BJTs. In an embodiment, the first BJT may be a NPN BJT and the second BJT may be a PNP BJT. In another embodiment, the third transistor may be a field effect transistor (FET).

Additional aspects of the disclosure may include embodiments of a personal alert safety system (PASS) for use in combination with a self-contained breathing apparatus (SCBA), comprising: a piezoelectric sound generator, a power supply, a piezoelectric controller, and a piezoelectric driver circuit comprising a push circuit comprising a first bipolar junction transistor (BJT), a second BJT, a third transistor, a first resistor, and a second resistor, wherein the first BJT may have a base lead coupled to an output of the piezocontroller, an emitter lead coupled to ground, and a collector lead coupled to a first lead of the first resistor, to an input of the third transistor, and to a base lead of the second BJT. In an embodiment, a second lead of the first resistor may be coupled to the power supply, a power input lead of the third transistor may be coupled to the power supply and an output of the third transistor may be coupled to a first lead of the second resistor and to a emitter lead of the second BJT, a second lead of the second resistor may be coupled to the piezoelectric sound generator, and the collector lead of the second BJT may be connected to ground. In an embodiment, the piezoelectric driver circuit may draw less than 5 mA in a no load state. In an embodiment, the power supply may receive power from at least one battery. In an embodiment, the power supply may comprise a voltage booster that receives power from the at least on battery. In an embodiment, the piezoelectric driver may drive the piezoelectric controller when the series voltage of the alkaline batteries is less than a predefined voltage that would otherwise not allow for operation under normal condition. In an embodiment, the predefined voltage may be four volts or less. In an embodiment, the third transistor may be a Darlington pair comprising two NPN BJTs in a single chip package. In an embodiment, the first BJT may be a NPN BJT and the second BJT may be a PNP BJT.

Other aspects of the disclosure may include embodiments of a self-contained breathing apparatus (SCBA) for use by emergency responders, comprising: a backpack; a bottle of gas secured to the backpack; and a personal alert safety system (PASS). The PASS may comprise a piezoelectric sound generator, a power supply, a piezoelectric controller, and a piezoelectric driver circuit comprising a push circuit comprising a first bipolar junction transistor (BJT), a second BJT, a third transistor, a first resistor, and a second resistor, wherein the first BJT may have a base lead coupled to an output of the piezocontroller, an emitter lead coupled to ground, and a collector lead coupled to a first lead of the first resistor, to an input of the third transistor, and to a base lead of the second BJT. In an embodiment, a second lead of the first resistor may be coupled to the power supply, a power input lead of the third transistor may be coupled to the power supply and an output of the third transistor may be coupled to a first lead of the second resistor and to a emitter lead of the second BJT, a second lead of the second resistor may be coupled to the piezoelectric sound generator, the collector lead of the second BJT may be connected to ground.

In an embodiment, the piezoelectric driver circuit may further comprise a pull circuit comprising a fourth BJT, a fifth BJT, a sixth transistor, a third resistor, and a fourth resistor, wherein the fourth BJT may have a base lead coupled to an output of the piezocontroller, an emitter lead coupled to ground, and a collector lead coupled to a first lead of the third resistor, to an input of the sixth transistor, and to a base lead of the fifth BJT. In an embodiment, a second lead of the third resistor may be coupled to the power supply, a power input lead of the sixth transistor may be coupled to the power supply and an output of the sixth transistor may be coupled to a first lead of the fourth resistor and to a emitter lead of the fifth BJT, a second lead of the fourth resistor may be coupled to the piezoelectric sound generator at an end opposite from the second end of the second resistor, and the collector lead of the fifth BJT may be connected to ground.

In an embodiment, the piezoelectric controller may pulse on and off at a frequency between about 2 KHz and about 4 KHz to cause the piezoelectric driver circuit to sound the piezoelectric sound generator. In an embodiment, the third transistor may be a Darlington pair comprising two NPN BJTs in a single chip package. In an embodiment, the first BJT may be a NPN BJT and the second BJT may be a PNP BJT. In an embodiment, the third transistor may be a field effect transistor (FET). In an embodiment, the first BJT may be a NPN BJT and the second BJT may be a PNP BJT and the third transistor may be a field effect transistor (FET).

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 3A and FIG. 3B illustrate an embodiment of a piezoelectric diaphragm;

FIGS. 4A-4C illustrates producing sound waves with a piezoelectric diaphragm;

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term “comprising” means including but not limited to, and should be interpreted in the manner it is typically used in the patent context;

The phrases “in one embodiment,” “according to one embodiment,” and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as “exemplary” or an “example,” it should be understood that refers to a non-exclusive example;

The terms “about” or approximately” or the like, when used with a number, may mean that specific number, or alternatively, a range in proximity to the specific number, as understood by persons of skill in the art field; and If the specification states a component or feature “may,” “can,” “could,” “should,” “would,” “preferably,” “possibly,” “typically,” “optionally,” “for example,” “often,” or “might” (or other such language) be included or have a characteristic, that particular component or feature is not required to be included or to have the characteristic. Such component or feature may be optionally included in some embodiments, or it may be excluded.

Figure 1A:
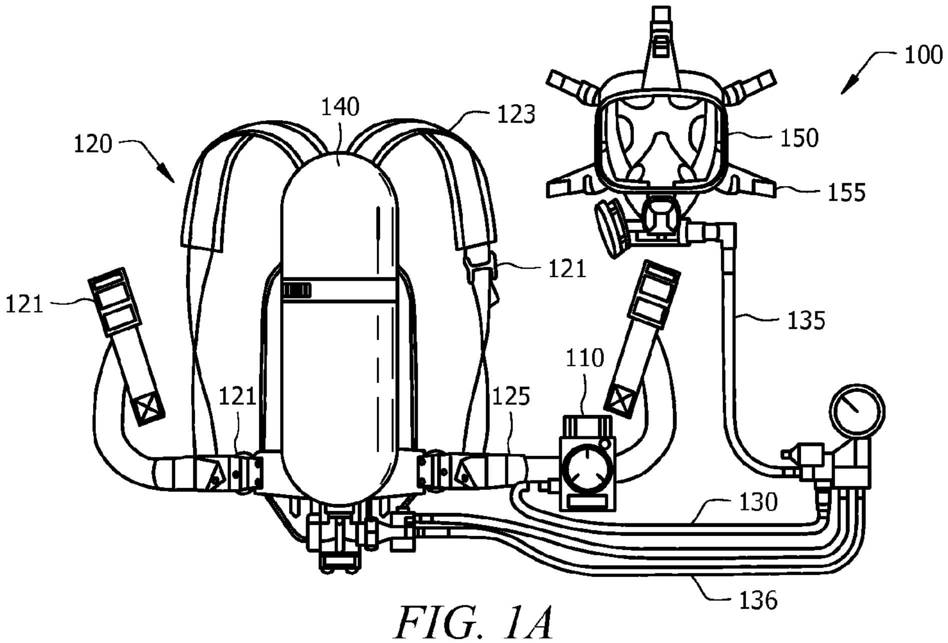
FIGS. 1A-1B illustrate an exemplary embodiment of a PASS device integrated into an SCBA unit.
Figure 1B:
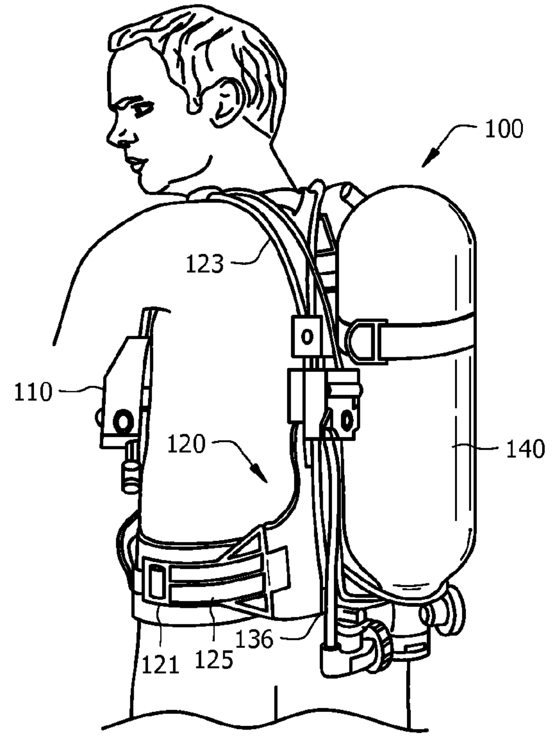

Embodiments relate generally to personal alert safety systems (PASS) as well as piezoelectric sound generators (also called piezos) which may be located within or packaged with a PASS device operable to alert others if a user is in danger. A personal alert safety system (PASS) device may be located anywhere on a user and may typically be attached to personal protective equipment, such as protective clothing or an SCBA, that the user may already be wearing based on the type of hazardous environment to be entered by the user. The diagrams of FIGS. 1A-1B show an exemplary embodiment where a PASS device 110 may be attached to an SCBA 100 that might be worn by a user. In the embodiments of FIGS. 1A-1B, the SCBA 100 may comprise a backpack 120 and a bottle of gas 140 secured to the backpack 120. The bottle of gas 140 may be operable to provide a user with oxygen for breathing in a dangerous and/or contaminated environment, such as a burning building for example. The SCBA 100 in the embodiment of FIGS. 1A-1B may also comprise a PASS device 110, which may be located in a position on the backpack 120 to allow for access by the user, which may be necessary if the PASS device could be manually activated, for example. The PASS device could be armed manually or automatically as well, and in some embodiments, the PASS device 110 may be integrated into an SCBA 100 such that the PASS device 110 may be initially armed when a user opens the air circuit 130 of a SCBA unit 100. In the exemplary embodiment of FIG. 1A, the PASS device 110 may be attached to the belt section 125 of the SCBA backpack 120, but in other embodiments, such as FIG. 1B, the PASS device 110 may be located in another position on the backpack 120, such as the shoulder strap 123. Either location may allow for easy access by a user. In some embodiments, the SCBA unit may further comprise other components, such as a mask 150, a head harness 155, air circuits 135 and 136, adjustment buckles 121 for the backpack 120, and other such components as would be understood by a person of skill in the art to be included in an SCBA unit.

Figure 2:
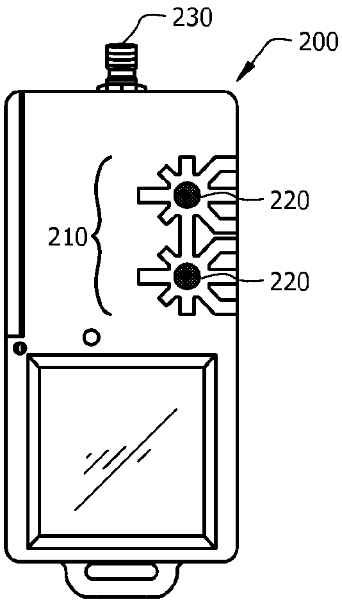
FIG. 2 illustrates an exemplary embodiment of a PASS device.

An exemplary embodiment of a PASS device 200 is shown in FIG. 2, wherein the PASS device 200 may comprise an audible alert system 210. The loud audible alert for the PASS typically may comprise one or more piezoelectric sound generators (or piezos) 220. The piezo(s) 220 may be controlled by an electrical circuit within the PASS device 200 which may be activated manually or automatically (for example, manually by the user pressing a button, or automatically by a motion sensing device that activates the PASS device when the user has not moved in a certain amount of time). The PASS device 200 may also comprise one or more connectors 230, which may allow for fluid communication between the PASS device 200 and an air circuit of an SCBA, for example. This connector 230 may allow the PASS device 200 to be automatically armed when air flow in the SCBA unit is initiated by a user.

A typical piezoelectric sound generator may comprise a piezoelectric diaphragm, which may be operable to create sound waves in response to an applied electric field. A typical embodiment of a piezoelectric diaphragm is shown in FIGS. 3A-3B, wherein FIG. 3A shows a top view and FIG. 3B shows a side view of the diaphragm 300. The diaphragm 300 may comprise a piezoelectric element 305, wherein the piezoelectric element 305 may comprise a piezoelectric ceramic plate 310 and two electrodes 320 on either side of the ceramic plate 310. The piezoelectric element 305 may additionally be attached to a metal plate 330 (for example, with adhesives), wherein the metal plate 330 may for example comprise brass, stainless steel, or another appropriate metal material.

As shown in the embodiment FIG. 4, applying direct current voltage between the two electrodes of the piezoelectric element 405 may cause mechanical distortion of the piezoelectric element 405 due to the piezoelectric effect (wherein mechanical distortion of a material may occur in response to an applied electrical field). Under the influence of a particular voltage, the piezoelectric element 405 may expand in a radial direction 415 while the metal plate 430 bonded to the piezoelectric element 405 may not expand or shrink but rather may bend as shown in FIG. 4A. When the voltage is changed, as shown in FIG. 4B, the piezoelectric element 305 may shrink in a radial direction 416 and therefore cause the metal plate 430 to bend in the opposite direction of the embodiment shown in FIG. 4A. Thus, when the voltage applied across the electrodes is alternated, the bending of the metal plate 430 shown in FIGS. 4A and 4B is alternated and repeated, as shown in FIG. 4C, producing sound waves in the air.

Figure 5:
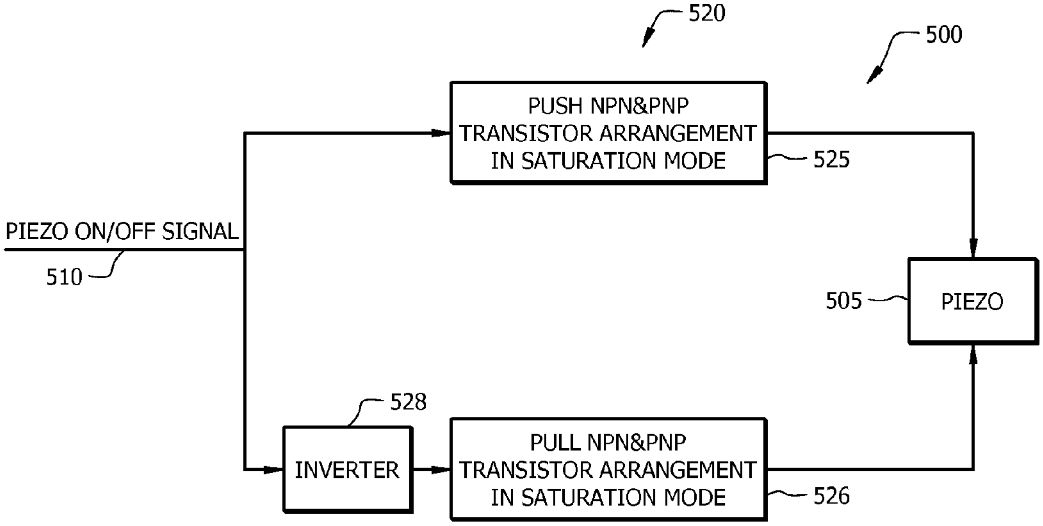
FIG. 5 illustrates an exemplary topology for a piezoelectric driver circuit of an alarm of a PASS device according to an embodiment of the disclosure.

FIG. 5 illustrates an embodiment of a driver topology 500 which may be used to activate and control a piezoelectric sound generator (or piezo) 505. As shown in FIG. 5, activation of the piezo 505 may involve a transistor based electrical circuit which may comprise an ON/OFF pulsed signal 510 (which may be provided by a piezocontroller) and a piezoelectric driver circuit 520 which may be operable to direct a voltage across the piezo 505 based on the ON/OFF pulse 510. In the embodiment of FIG. 5, the driver circuit 520 may comprise a push circuit 525 operable to direct a voltage across the speaker 505. In an embodiment, the driver circuit 520 may additionally comprise a pull circuit 526 which may also be operable to direct a voltage across the speaker 505 but typically in the opposite direction of the push circuit 525. The pull circuit 526 may comprise an inverter 528 operable to invert the ON/OFF signal, such that when the push circuit 525 is activated by an ON signal, the pull circuit 526 is not activated (that is, receives an OFF signal) and vice versa. In an embodiment, the inverter 528 may be operable to ensure that a bipolar AC power is applied across the piezo.

Figure 6:
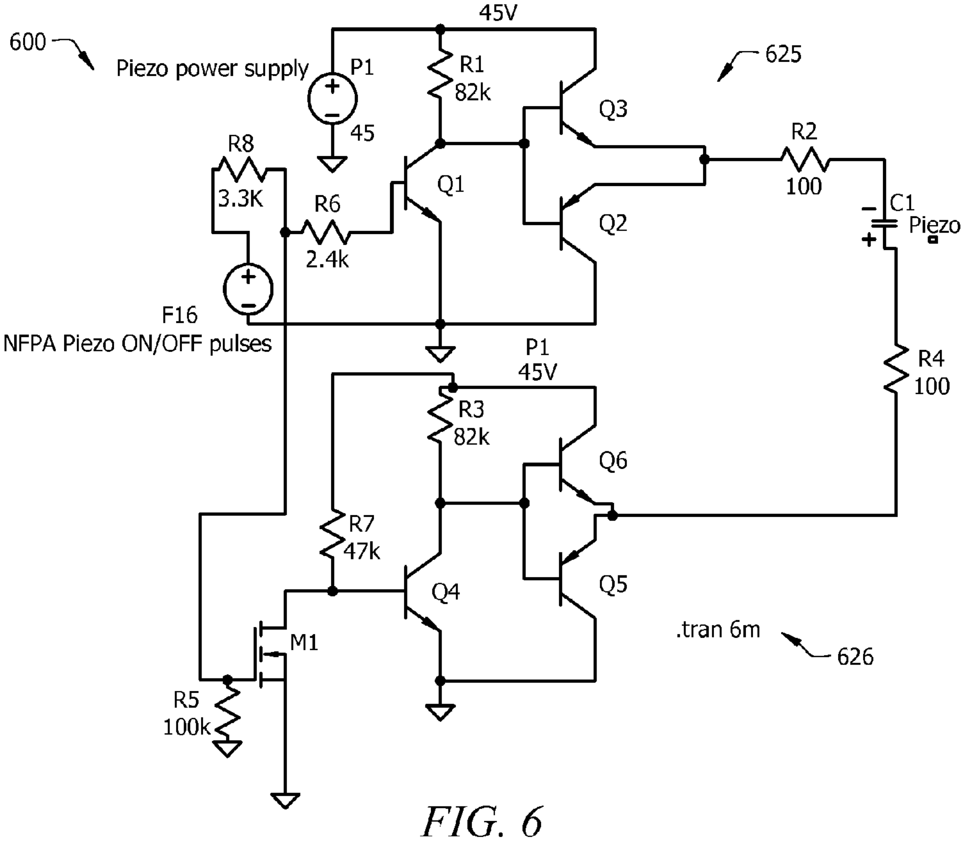
FIG. 6 illustrates a schematic diagram of a piezoelectric driver circuit of an alarm of a PASS device according to an embodiment of the disclosure.

FIG. 6 shows a detailed schematic of an embodiment of a piezoelectric driver circuit 600 (as shown in FIG. 5, 520) for an alarm of a PASS device. A piezocontroller F16 may direct an ON/OFF signal through the driver circuit 600. The driver circuit 600 may comprise a power supply P1, which may comprise one or more batteries and may also comprise a separate power booster circuit for the power supply voltage. The push circuit 625 of the a piezoelectric driver circuit 600 may comprise a first bipolar junction transistor (BJT) Q1, a second BJT Q2 and a third transistor Q3 (which may comprise one or more BJTs, a field effect transistor, or a Darlington pair, for example) and may further comprise a first resistor R1 and a second resistor R2. In an embodiment, the first BJT Q1 may be an NPN-type transistor and may have a base lead coupled to an output of the piezocontoller F16, an emitter lead coupled to ground, and a collector lead coupled to the following: a first lead of the first resistor R1, an input of the third transistor Q3, and a base lead of the second BJT Q2. In an embodiment, the coupling between the base lead of the first BJT and the output of the piezocontroller F16 may comprise the presence of protection resistors. In an embodiment, the second BJT Q2 may be a PNP-type transistor and the third transistor Q3 may be an NPN-type transistor. In an embodiment, the second lead of the first resistor R1 may be coupled to the power supply P1. Further, a power input lead of the third transistor Q3 may be coupled to the power supply P1, and an output of the third transistor Q3 may be coupled to a first lead of the second resistor R2 and to an emitter lead of the second BJT Q2. Additionally, a second lead of the second resistor R2 may be coupled to the piezoelectric sound generator C1, and the collector lead of the second BJT Q2 may be connected to ground.

The pull circuit 626 of the piezoelectric driver circuit 600 may comprise a fourth BJT Q4, a fifth BJT Q5, a sixth transistor Q6 (which may comprise one or more BJTs, a field effect transistor, or a Darlington pair, for example) and may further comprise a third resistor R3 and a fourth resistor R4. In an embodiment, the fourth BJT Q4 may be an NPN-type transistor and may have a base lead coupled to the drain of the MOSFET M1, an emitter lead coupled to ground, and a collector lead coupled to the following: a first lead of the third resistor R3, an input of the sixth transistor Q6, and a base lead of the fifth BJT Q5. In an embodiment, the fifth BJT Q5 may be a PNP-type transistor, and the sixth BJT Q6 may be an NPN-type transistor, one or more BJTs, a field effect transistor, or a Darlington pair. In an embodiment, the second lead of the third resistor R3 may be coupled to the power supply P1. Further, a power input lead of the sixth transistor Q6 may be coupled to the power supply P1, and an output of the sixth transistor Q6 may be coupled to a first lead of the fourth resistor R4 and to an emitter lead of the fifth BJT Q5. Additionally, a second lead of the fourth resistor R4 may be coupled to the piezoelectric sound generator C1, and the collector lead of the fifth BJT Q5 may be connected to ground.

Additionally, in an embodiment, the electronic circuit may comprise an inverter M1 located between the output of the piezocontroller F16 and the base lead of the fourth BJT Q4, operable to invert the ON/OFF pulses coming from the piezocontroller F16. That is, when the piezocontroller F16 pulses ON, the inverter M1 may change the pulse that is sent to the pull circuit 626 to OFF and vice versa. The driver circuit 600 may also optionally comprise additional resistors R5, R6, R7 and R8. R8 may be the current limiting resistor for M1 and R6 may ensure that the voltage available for M1 is not limited by base emitter junction of Q1. The values of R8 and R6 may be decided based on the Vgs (gate-to-source voltage) threshold of the inverter M1 and the ON state voltage of the pulse. In another embodiment, the left end of R6 may be connected to the pulse directly (left end of R8/positive of F16) while the right end remains connected to the base of the first BJT Q1. Resistor R7 may provide bias for the fourth BJT Q4 and may be connected between power supply P1 and the base of Q4 and the drain of the inverter M1.

In an embodiment, when the piezoelectric controller F16 is activated (which may be manually or automatically activated by a separate circuit), the controller F16 pulses ON and OFF (typically at a frequency between about 2 KHz and about 4 KHz) to cause the piezoelectric driver circuit to sound the piezoelectric sound generator C1. This may be accomplished in a push-pull configuration comprising a push circuit 625 and a pull circuit 626, as mentioned above. In an embodiment shown in FIG. 6, when the piezocontroller F16 pulses ON, the first BJT Q1 of the push circuit 625 may enter into saturation mode. This may cause the voltage at the base of the second BJT Q2 and at the base of the third transistor Q3 to become equal to the saturation voltage of the first BJT Q1, which may be small when compared to the voltage at the junction between the second BJT Q2 and the third transistor Q3. In an embodiment, the saturation voltage of the first BJT Q1 may be between about 50 mV and about 200 mV. This may allow the third transistor Q3 to remain in OFF condition and the second BJT Q2 to remain in ON condition. The voltage at the common emitter of the second BJT Q2 and the third transistor Q3 may be equal to the collector emitter saturation voltage of the first BJT Q1 plus the base emitter saturation voltage of the second BJT Q2, which may typically be less than 1 V.

Figure 7:
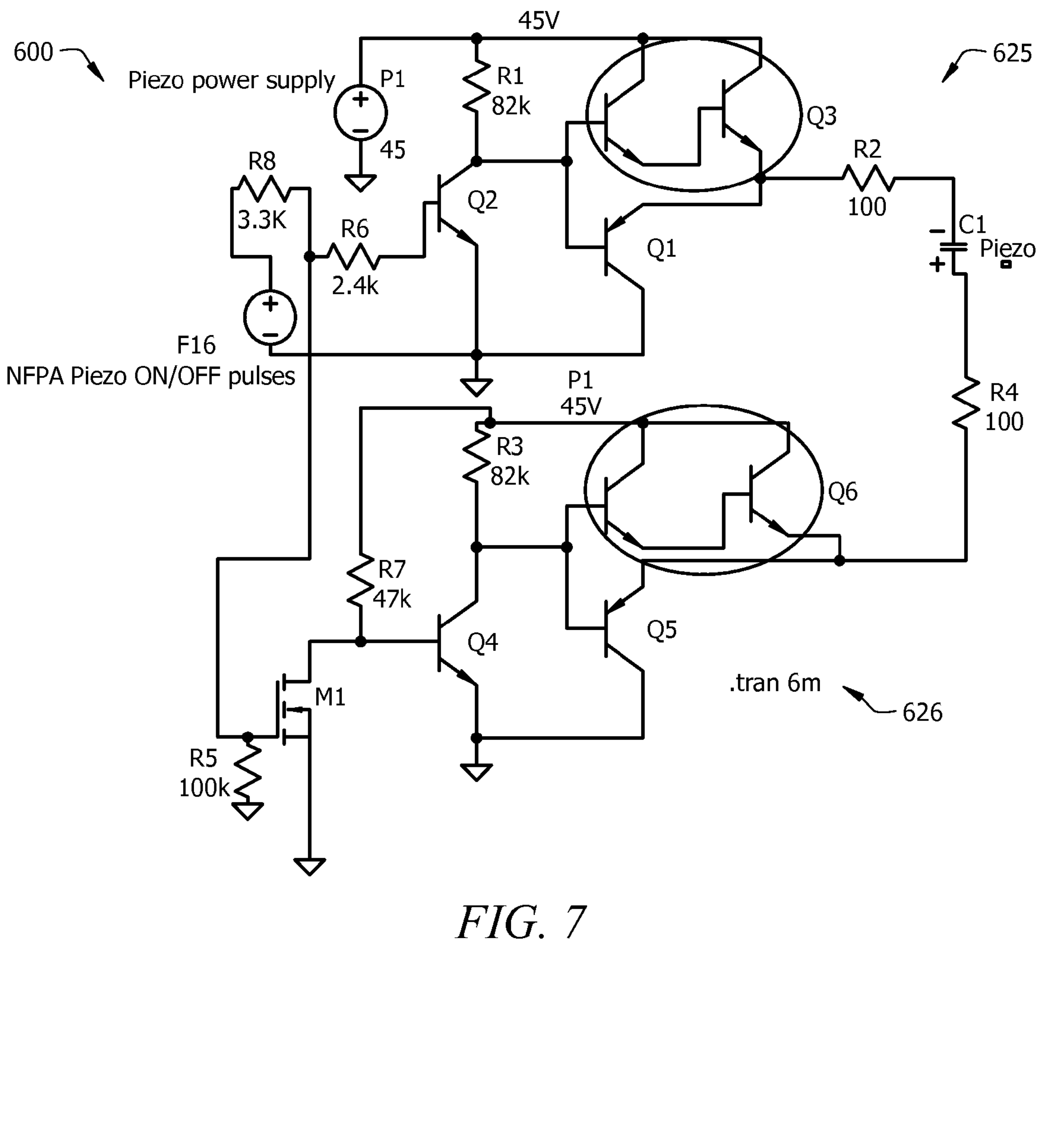
FIG. 7 illustrates a schematic diagram of a piezoelectric driver circuit of an alarm of a PASS device that includes Darlington pairs according to an embodiment of the disclosure.

In an embodiment, when the piezocontroller F16 pulses OFF, Q1 may enter into an off mode. This may enable the voltage at the bases of the second BJT Q2 and the third transistor Q3 to reach a value that is proximate to the supply voltage, which may thereby cause the third transistor Q3 to conduct and the second BJT Q2 to turn OFF. In the embodiment of FIG. 7, the third transistor Q3 may comprise a Darlington pair, wherein two transistors (which may be NPN BJTs) may be coupled in a single chip package and may function as one transistor. In another embodiment, the Darlington pair may be made of two NPN BJTs or one NPN and one PNP BJT. In another embodiment, shown in FIG. 8, the third transistor Q3 may comprise a field effect transistor. The values shown in FIGS. 6-8 for the resistors and the power supply may be considered representative of possible operational values for the piezoelectric driver circuit. However, other values may also be used in the operation of an embodiment of the piezoelectric driver circuit.

The pull circuit 626 may operate in a similar manner to the push circuit 625, however the inverter M1 may change the polarity of the pulse from the piezocontroller F16 that is sent to the pull circuit 626 from ON to OFF and vice versa, such that when the push circuit 625 is "on" (that is, the push circuit 625 is responding to an ON pulse) the pull circuit 626 is "off" (that is, the pull circuit 626 is responding to an OFF pulse) and when the push circuit 625 is "off" (that is, the push circuit is responding to an OFF pulse) the pull circuit 626 is "on" (that is, the pull circuit is responding to an ON pulse). In an embodiment, the polarity across the piezoelectric sound generator C1 may be such that the negative side is connected to the push circuit 625 and the positive side is connected to the pull circuit 626. Thus, the piezo C1 may be stimulated with alternating voltages of approximately −40 volts (which may be supplied by the push circuit 625) and approximately +40 volts (which may be supplied by the pull circuit 626) which may be caused by the alternation of an ON/OFF pulse created by the piezocontroller F16.

In an embodiment, when the piezocontroller F16 pulses ON, the inverter M1 may invert the pulse, and the fourth BJT Q4 of the pull circuit 626 may enter into OFF mode. This may cause the voltage at the base of the fifth BJT Q5 and at the base of the sixth transistor Q6 to become approximately equal to the supply voltage. The voltage at the common emitter of the fifth BJT Q5 and the sixth transistor Q6 may be approximately equal to the supplied voltage from the power supply P1 (which may be about 40 volts) minus the voltage across the sixth transistor Q6 (which may be relatively small, making the voltage at the common emitter of the fifth BJT Q5 and the sixth transistor Q6 approximately equal to the supplied voltage from the power supply P1). Additionally, the voltage at the positive end of the piezo C1 will be approximately equal to the voltage at the common emitter of the fifth BJT Q5 and the sixth transistor Q6 (which may be approximately 40 volts) minus the voltage across the fourth resistor R4 (which may be relatively small, making the voltage at the piezo C1 approximately equal to the supplied voltage from the power supply P1).

In an embodiment, when the piezocontroller F16 pulses OFF, the inverter M1 may invert the pulse to ON, Q4 may enter into a saturation mode. This may enable current to flow from the emitter of the fifth BJT Q5 to the base, causing the fifth BJT Q5 to enter into saturation mode. When the fifth BJT Q5 enters saturation mode, the voltage at the emitter of the fifth BJT Q5 and the emitter of the sixth transistor Q6 (and thus the voltage going to the piezo) may become equal to the saturation voltage of the fifth BJT Q5, which may be approximately 1 volt. In the embodiment of FIG. 7, the sixth transistor Q6 may comprise a Darlington pair, wherein two transistors (which may be NPN BJTs) may be housed in a single chip package and may function as one transistor. In another embodiment, shown in FIG. 8, the sixth transistor Q6 may comprise a field effect transistor. The values shown in FIGS. 6-8 for the resistors and the power supply may be considered representative of possible operational values for the piezoelectric driver circuit. However, other values may also be used in the operation of an embodiment of the piezoelectric driver circuit.

In an embodiment, the power supply may comprise at least one battery and may also comprise a booster circuit operable to amplify the voltage supplied by the at least one battery. In an embodiment, the at least one battery may comprise around three or four alkaline batteries. In an embodiment, the voltage supplied to the driver circuit by the power supply may be more than about 40 volts. In another embodiment, when the voltage supplied by the power supply to the driver circuit is less than about 3 volts (such as when the batteries may be losing power or dying), the driver circuit may drive the piezoelectric controller 510 (as shown in FIG. 5), wherein the piezo alarm may sound at a lower dB level. In an embodiment, the driver circuit may avoid alarm reset when the power supply is less than about 3V, allowing the alarm to sound even at a low power supply. In an embodiment, the piezoelectric driver circuit 520 may draw less than about 5 mA in a no-load state, wherein no load refers to a state when the piezocontroller is not activated. In another embodiment, the driver circuit 520 may draw less than about 2 mA in a no-load state. Thus, a no-load current consumption may be a measure of only the current consumption of the driver, and not the piezoelectric speaker, and therefore may be determined by the design of the driver circuit. This may allow for longer battery life for the PASS device, because the driver circuit may not drain a large amount of power from the batteries when the alarm is not activated, based on the low no-load current consumption.

Figure 8:
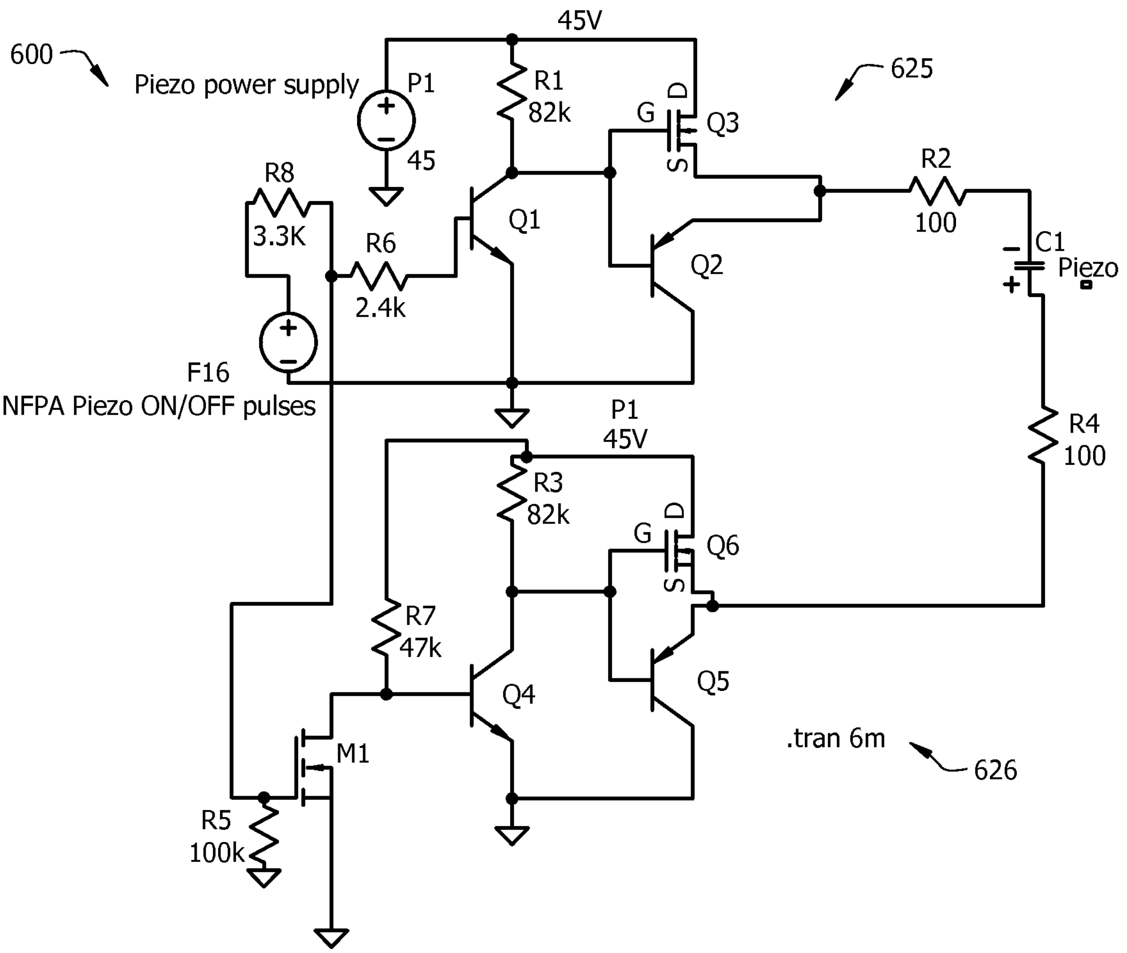
FIG. 8 illustrates a schematic diagram of a piezoelectric driver circuit of an alarm of a PASS device that includes field effect transistors according to an embodiment of the disclosure.
Figure 9:
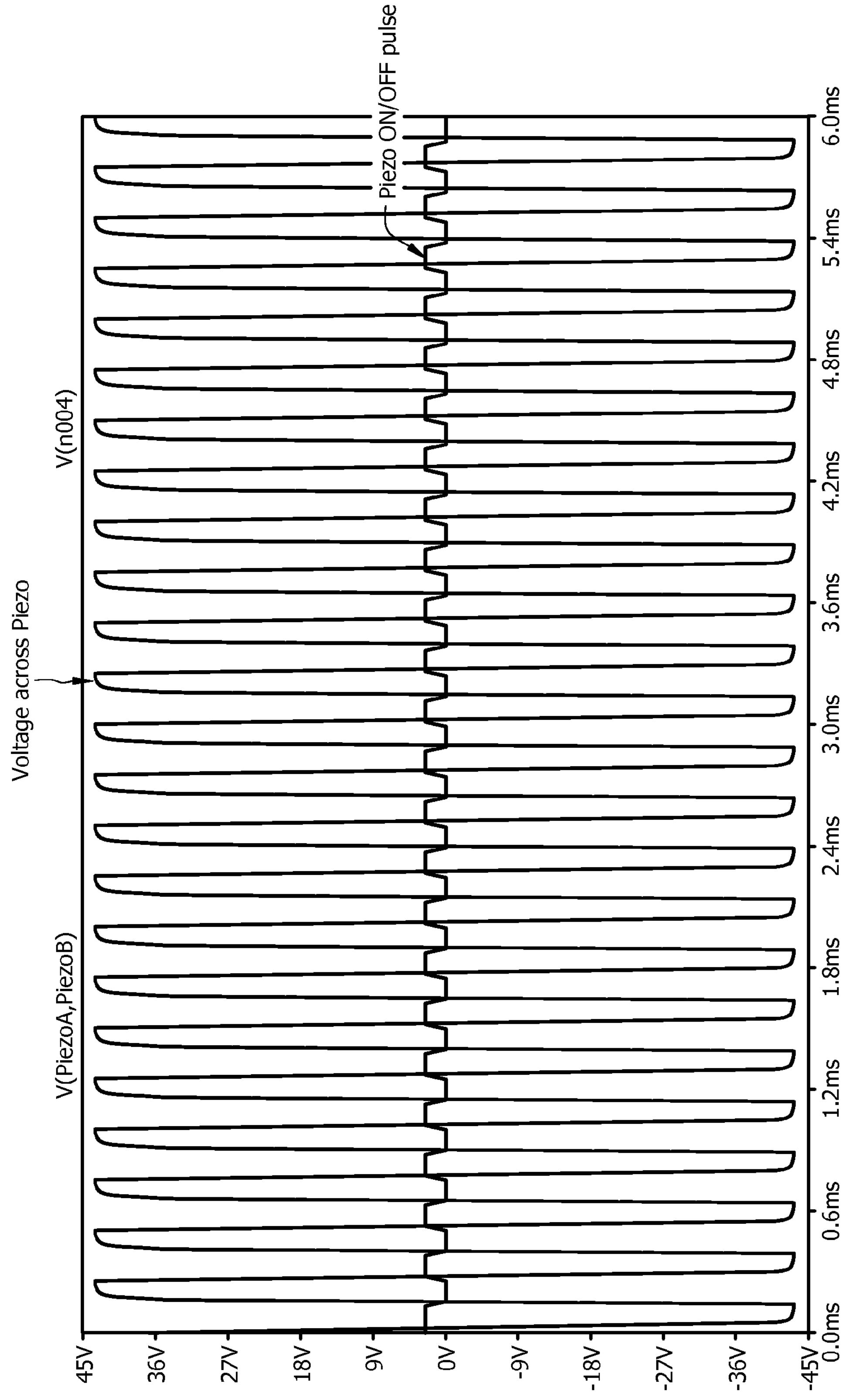
FIG. 9 illustrates a voltage reading across a piezoelectric sound generator in response to a pulse from a piezocontroller according to an embodiment of the disclosure.

In the embodiments shown in FIGS. 6-8, the piezoelectric driver circuit may be designed such that there is a polarity across the piezoelectric sound generator C1. In the embodiment of FIGS. 6-8, the polarity may be such that the negative side is connected to the push circuit 625 and the positive side is connected to the pull circuit 626. As shown in the graph of FIG. 9, when the piezocontroller pulses ON, it is at about 3V, and when it pulses OFF, it is at about zero volts or ground. The corresponding graph showing the voltage across the piezo shows that when the piezocontroller pulses ON, the voltage across the piezo is between approximately +40 and +45 volts (i.e. the voltage is directed across the piezo in a positive direction at about 40-45 volts). The voltage amount may be determined by the voltage coming from the power supply. Additionally, the graph shows that when the piezocontroller pulses OFF, the voltage across the piezo is between approximately −40 and −45 volts (i.e. the voltage is directed across the piezo in a negative direction at about 40-45 volts). The graph in FIG. 9 illustrates one embodiment of the operation of a piezocontroller to control a piezoelectric sound generator, wherein the piezocontroller pulses may alternate between ON and OFF; however in other embodiments of operation, voltage ranges greater than approximately 40-45 volts and/or less than approximately 40-45 volts may be used. The reading shown in FIG. 9 may correspond to the polarity convention shown in FIGS. 6-8 across the piezo speaker.

In an embodiment, the third and sixth transistors Q3 and Q6 as shown in FIGS. 6-8 may be considered to be three-lead semiconductors or three-lead semiconductor switches, wherein a three-lead semiconductor or semiconductor switch may comprise one or more bipolar junction transistors (BJTs), one or more field effect transistors, or one or more Darlington pairs, for example. In other words, any design which may be considered to be a three-lead semiconductor or three-lead semiconductor switch may function in the place of one or both of the third and sixth transistors Q3 and Q6 for the embodiments shown in FIGS. 6-8. In an embodiment, the third and sixth transistors Q3 and Q6 may also comprise two separate transistors connected in a Darlington fashion.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a “Field,” the claims should not be limited by the language chosen under this heading to describe the so-called field. Further, a description of a technology in the “Background” is not to be construed as an admission that certain technology is prior art to any invention(s) in this disclosure. Neither is the “Summary” to be considered as a limiting characterization of the invention(s) set forth in issued claims. Furthermore, any reference in this disclosure to “invention” in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of Use of the term “optionally,” “may,” “might,” “possibly,” and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A self-contained breathing apparatus (SCBA) for use by emergency responders, comprising:

a backpack;

a bottle of gas secured to the backpack; and a personal alert safety system (PASS) comprising a piezoelectric sound generator,
a power supply,
a piezoelectric controller, and
a piezoelectric driver circuit comprising a push circuit comprising a first bipolar junction transistor (BJT), a second BJT, a third transistor, a first resistor, and a second resistor,
wherein the first BJT has a base lead coupled to an output of the piezocontroller, an emitter lead coupled to ground, and a collector lead coupled to a first lead of the first resistor, to an input of the third transistor, and to a base lead of the second BJT,
wherein a second lead of the first resistor is coupled to the power supply,
wherein a power input lead of the third transistor is coupled to the power supply and an output of the third transistor is coupled to a first lead of the second resistor and to an emitter lead of the second BJT,
wherein a second lead of the second resistor is coupled to the piezoelectric sound generator,
wherein the collector lead of the second BJT is connected to ground.

2. The self-contained breathing apparatus of claim 1, wherein the piezoelectric driver circuit further comprises a pull circuit comprising a fourth BJT, a fifth BJT, a sixth transistor, a third resistor, and a fourth resistor,
wherein the fourth BJT has a base lead coupled to an output of the piezocontroller through an inverter, an emitter lead coupled to ground, and a collector lead coupled to a first lead of the third resistor, to an input of the sixth transistor, and to a base lead of the fifth BJT,
wherein a second lead of the third resistor is coupled to the power supply,
wherein a power input lead of the sixth transistor is coupled to the power supply and an output of the sixth transistor is coupled to a first lead of the fourth resistor and to an emitter lead of the fifth BJT,
wherein a second lead of the fourth resistor is coupled to the piezoelectric sound generator at an end opposite from the second end of the second resistor,
wherein the collector lead of the fifth BJT is connected to ground.

3. The self-contained breathing apparatus of claim 1, wherein the third transistor is a Darlington pair.

4. The self-contained breathing apparatus of claim 3, wherein the third transistor is a Darlington pair comprising two NPN BJTs.

5. The self-contained breathing apparatus of claim 4, wherein the first BJT is a NPN BJT and the second BJT is a PNP BJT.

6. The self-contained breathing apparatus of claim 1, wherein the third transistor is a field effect transistor (FET).

7. A personal alert safety system (PASS) for use in combination with a self-contained breathing apparatus (SCBA), comprising:
a piezoelectric sound generator,
a power supply,
a piezoelectric controller, and
a piezoelectric driver circuit comprising a push circuit comprising a first bipolar junction transistor (BJT), a second BJT, a third transistor, a first resistor, and a second resistor,
wherein the first BJT has a base lead coupled to an output of the piezocontroller, an emitter lead coupled to ground, and a collector lead coupled to a first lead of the first resistor, to an input of the third transistor, and to a base lead of the second BJT,
wherein a second lead of the first resistor is coupled to the power supply,
wherein a power input lead of the third transistor is coupled to the power supply and an output of the third transistor is coupled to a first lead of the second resistor and to an emitter lead of the second BJT,
wherein a second lead of the second resistor is coupled to the piezoelectric sound generator,
wherein the collector lead of the second BJT is connected to ground.

8. The personal alert safety system of claim 7, wherein the piezoelectric driver circuit draws less than 5 mA in a no-load state.

9. The personal alert safety system of claim 7, wherein the power supply receives power from at least one battery.

10. The personal alert safety system of claim 9, wherein the power supply is a voltage booster that receives power from the at least one battery.

11. The personal alert safety system of claim 10, wherein the piezoelectric driver drives the piezoelectric controller when the series voltage of the at least one battery is less than a predefined voltage that would otherwise not allow for operation under normal condition.

12. The self-contained breathing apparatus of claim 7, wherein the third transistor is a Darlington pair.

13. The personal alert safety system of claim 12, wherein the third transistor is a Darlington pair comprising two NPN BJTs in a single chip package.

14. The personal alert safety system of claim 7, wherein the first BJT is a NPN BJT and the second BJT is a PNP BJT.

15. A self-contained breathing apparatus (SCBA) for use by emergency responders, comprising:
a backpack;
a bottle of gas secured to the backpack; and
a personal alert safety system (PASS) comprising
a piezoelectric sound generator,
a power supply,
a piezoelectric controller, and
a piezoelectric driver circuit comprising a push circuit comprising
a first bipolar junction transistor (BJT), a second BJT, a third transistor, a first resistor, and a second resistor,
wherein the first BJT has a base lead coupled to an output of the piezocontroller, an emitter lead coupled to ground, and a collector lead coupled to a first lead of the first resistor, to an input of the third transistor, and to a base lead of the second BJT,
wherein a second lead of the first resistor is coupled to the power supply,
wherein a power input lead of the third transistor is coupled to the power supply and an output of the third transistor is coupled to a first lead of the second resistor and to an emitter lead of the second BJT,
wherein a second lead of the second resistor is coupled to the piezoelectric sound generator,
wherein the collector lead of the second BJT is connected to ground,
and the piezoelectric driver circuit further comprising a pull circuit comprising
a fourth BJT, a fifth BJT, a sixth transistor, a third resistor, and a fourth resistor,
wherein the fourth BJT has a base lead coupled to an output of the piezocontroller, an emitter lead coupled to ground, and a collector lead coupled to a first lead of the third resistor, to an input of the sixth transistor, and to a base lead of the fifth BJT, wherein a second lead of the third resistor is coupled to the power supply, wherein a power input lead of the sixth transistor is coupled to the power supply and an output of the sixth transistor is coupled to a first lead of the fourth resistor and to an emitter lead of the fifth BJT, wherein a second lead of the fourth resistor is coupled to the piezoelectric sound generator at an end opposite from the second end of the second resistor, wherein the collector lead of the fifth BJT is connected to ground.

16. The self-contained breathing apparatus of claim 15, wherein the piezoelectric controller pulses on and off at a frequency between about 2 KHz and about 4 KHz to cause the piezoelectric driver circuit to sound the piezoelectric sound generator.

17. The self-contained breathing apparatus of claim 15, wherein the third transistor is a Darlington pair comprising two NPN BJTs in a single chip package.

18. The self-contained breathing apparatus of claim 15, wherein the first BJT is a NPN BJT and the second BJT is a PNP BJT.

19. The self-contained breathing apparatus of claim 15, wherein the third transistor is a field effect transistor (FET).

20. The self-contained breathing apparatus of claim 15, wherein the first BJT is a NPN BJT and the second BJT is a PNP BJT and wherein the third transistor is a field effect transistor (FET).

* * * * *